US010492758B2

(12) United States Patent
De Beni et al.

(10) Patent No.: US 10,492,758 B2
(45) Date of Patent: Dec. 3, 2019

(54) DEVICE AND METHOD FOR GUIDING SURGICAL TOOLS

(75) Inventors: Stefano De Beni, Genoa (IT); Marco Maccio', Genoa (IT)

(73) Assignee: Esaote, S.p.A., Genoa (IT)

( * ) Notice: Subject to any disclaimer, the term of this patent is extended or adjusted under 35 U.S.C. 154(b) by 507 days.

(21) Appl. No.: 12/508,266

(22) Filed: Jul. 23, 2009

(65) Prior Publication Data

US 2010/0022871 A1    Jan. 28, 2010

(30) Foreign Application Priority Data

Jul. 24, 2008    (IT) .............................. GE2008A0064

(51) Int. Cl.
| | | |
|---|---|---|
| *A61B 8/00* | (2006.01) | |
| *A61B 8/08* | (2006.01) | |
| *A61B 90/00* | (2016.01) | |
| *A61B 34/20* | (2016.01) | |

(52) U.S. Cl.
CPC .......... *A61B 8/4245* (2013.01); *A61B 8/0833* (2013.01); *A61B 8/0841* (2013.01); *A61B 8/483* (2013.01); *A61B 8/4254* (2013.01); *A61B 34/20* (2016.02); *A61B 2090/364* (2016.02)

(58) Field of Classification Search
CPC .... A61B 5/06; A61B 19/5225; A61B 19/5244
USPC ....................................................... 600/424
See application file for complete search history.

(56) References Cited

U.S. PATENT DOCUMENTS

| 6,505,065 B1* | 1/2003 | Yanof ................... A61N 5/103 600/103 |
|---|---|---|
| 2001/0044578 A1* | 11/2001 | Ben-Haim et al. ........... 600/424 |
| 2002/0156376 A1* | 10/2002 | Wang .................. A61B 8/0833 600/439 |
| 2003/0135119 A1* | 7/2003 | Lee et al. ....................... 600/461 |
| 2004/0059217 A1* | 3/2004 | Kessman et al. ............. 600/424 |

(Continued)

FOREIGN PATENT DOCUMENTS

| EP | 1167996 A1 | 1/2002 |
|---|---|---|
| EP | 1681019 A1 | 7/2006 |

(Continued)

OTHER PUBLICATIONS

European Search Report from EP 09165926 dated Aug. 21, 2009.
Written Opinon from Application No. ITGE20080064 dated May 18, 2009.

*Primary Examiner* — Jonathan Cwern
(74) *Attorney, Agent, or Firm* — Woodard, Emhardt, Henry, Reeves & Wagner, LLP

(57) ABSTRACT

A device and method for guiding surgical tools by ultrasonic imaging having means for acquiring a time sequence of 3D ultrasonic images of a target area, means for determining and tracking the position and orientation of a surgical tool and means for defining the direction of a characteristic axis of the tool corresponding to the detected position and orientation of the tool. The device further having means for determining the position of a working end of the tool along the characteristic axis, means for determining the relative position in space of each 3D image and the direction of the characteristic axis corresponding to each 3D image, and means for generating a 2D image defined by an image plane that intersects the corresponding 3D image of said time sequence.

24 Claims, 3 Drawing Sheets

(56) References Cited

U.S. PATENT DOCUMENTS

2004/0193042 A1* 9/2004 Scampini et al. ............ 600/424
2008/0287783 A1* 11/2008 Anderson ..................... 600/429
2009/0093715 A1* 4/2009 Downey .............. A61B 8/0833
                                                       600/437
2009/0275823 A1* 11/2009 Ayati et al. ................... 600/424

FOREIGN PATENT DOCUMENTS

WO    WO 2005/039391 A      5/2005
WO    WO 2006/067676 A      6/2006
WO    WO 2006067676 A2 *    6/2006

* cited by examiner

DEVICE AND METHOD FOR GUIDING SURGICAL TOOLS

CROSS-REFERENCE TO RELATED APPLICATIONS

This application claims the foreign priority benefit of Italian Patent Application No. GE2008A000064, filed Jul. 24, 2008, which is hereby incorporated by reference.

BACKGROUND

The invention relates to a device and a method for guiding surgical tools by ultrasonic imaging. The device and method of the invention are particularly applicable to ultrasonically guided minimally invasive surgery and are especially aimed at avoiding the use of the known biopsy kits. The main applications are in the surgical field (biopsy, infiltrations, ablations, etc.).

In the past, minimally invasive surgery mainly relied on CT imaging, followed by free-hand needle introduction based on the previously acquired images. The advent of ultrasonic imaging machines and biopsy kits allowing biopsy needles to be imaged as they were inserted in the tissue did not solve all the needle guiding problems. In many cases, CT imaging is still used because certain types of diseases cannot be imaged by ultrasound (lungs, bones), wherefore the ultrasonically guided biopsy kit is of no effective help.

Nonetheless, there undoubtedly exists the need for a needle insertion supporting tool allowing to evaluate beforehand the path of the needle, and hence its position relative to the probe plane and its path before actual insertion, because such tool would provide remarkable help, as well as technological advantage.

Also, there currently exist neurosurgery navigation systems as well as other virtual navigation systems combined with ultrasonic imaging methods. Nevertheless, these systems require an image of a pre-acquired volume, i.e. acquired prior to the surgical procedure, to be always associated with the surgical tool or ultrasonic probe.

Document WO2006/067676, discloses a method for visualizing the position of an interventional device involving the acquisition of images of an area of interest from an object displaying multiple planes that intersect. The intersection defines the position of the interventional device and the planes that identify the position of the interventional device are displayed as bounding planes. These bounding planes are displayed in a multi-dimensional display, where each plane is only rendered up to where it intersects another plane. Thanks to this only relevant portions of the data are displayed, thereby increasing the readability of the displayed image.

From the above document it is clear that at least a 3D image of the intervention area is acquired prior of carrying out the intervention and the intervention tool tracking and imaging. The orientation and the position of the tool are determined by the tracking data. The tracking system is registered with the acquired and stored 3D image data and the tracking data are used to determine the bounding planes and the image information along these bonding planes from the previously acquired 3D image data. It is important to consider that in this case volumetric (3D image data of the patient is acquired only once prior of the carrying out of the intervention, so that the determination of the interventional tool in the following intervention due to the tracking data is referred to the volumetric image data which has been acquired at an earlier instant. Considering patient movements and also natural movements of the tissues due to heart beats, breathing, etc., the reliability of the information about the relative position of the tool relatively to the a target object is relatively low.

Document WO2005/039391, seems to have considered this problem and suggests a way of solving the above problem. A method is disclosed for assisting a user in guiding a medical instrument to a subsurface target site in a patient. The method generates at least one intraoperative ultrasonic image. The method indicates a target site on the ultrasonic image and determines a 3-D coordinates of the target site in a reference coordinate system. The method tracks the position of the instrument in the coordinate system, projects onto a display device a view field as seen from the position with respect to the tool in the reference system and projects onto the displayed view field indicia of the target site corresponding to the position. By observing the indicia the user can guide the instrument toward the target site by moving the instrument so that the indicia are placed or held in a given state in the displayed filed of view.

The above disclosed method requires an endoscope for determining the images of the target site. Means for acquiring a pre-interventional 3D image which is the reference image, means for acquiring ultrasound images, an interventional tool, means for tracking the ultrasound probe, the endoscope and the interventional tool and means for registering the data from the pre-interventional volumetric image with the endoscopic image, with the ultrasound image data and with the tracking data.

The system is complex and in order to generate images corresponding to the views of a human user as placed on the tip of the tool and looking in direction of vied corresponding to a certain tool orientation, the endoscopic image is needed. Furthermore this image is a video image and not an ultrasound image which could help in see what is behind a certain surface. The ultrasound images displayed are along planes which comprise also the interventional tool image. The computational burden is considerable since the computation shall provide for registering video images of the endoscope, tracking data of the interventional tool and of the endoscope and of the ultrasound probe and the pre-intervention volumetric images and has to continuously generate images which are recalculated basing on the new position of the tool and of the target.

Each of the above methods require a pre-interventional volumetric image acquisition, which image data are used for determining the relative position of the tool to the anatomy of the interventional district and to a certain target site and cannot thus considered pure real-time methods, since a high influence in the image showing the relative position of target site and tool is given by this fact and the position inaccuracy due to systemic physiological tissue movements is still given to a high rate.

The invention has the object of providing a device and a method for guiding surgical tools by ultrasonic imaging which, using simple and inexpensive arrangements, can obviate the limitations of current surgical tool guiding and/or virtual navigation systems, while providing a better, easier and more intuitive control of the tool, with higher accuracy and in a substantially real-time mode, without involving any hardware extension image quality degradation or excessively longer scanning and processing times.

One embodiment of the invention fulfills the above object by providing a device as described hereinbefore, which comprises:

a) means for acquiring in real-time a time sequence of 3D ultrasonic images of a target area;

b) means for the contemporary real-time tracking the position and orientation of a surgical tool and means for defining in real-time the position or direction of a characteristic axis of the tool corresponding to the detected position and orientation of the tool;

c) means for determining in real-time the position of a working or functional end of the tool along said direction or said characteristic axis;

d) means for determining the relative position in space of each real-time 3D image and the real-time direction or characteristic axis of the tool corresponding to each real-time 3D image;

e) means for generating, for one or more of the real-time 3D images acquired in a time sequence, a real-time 2D image defined by an image plane that intersects the corresponding real-time 3D image of said time sequence, which real-time 2D image plane has a predetermined inclination relative to the direction or the characteristic axis of the tool determined in real-time and a predetermined distance from the working end of the tool with reference to the said orientation and position of the tool upon acquisition of the corresponding real-time 3D image, said real-time 2D image being generated using the real-time image data of the corresponding real-time 3D image of the time sequence of real-time 3D images;

g) the inclination of said real-time 2D image plane relative to the direction or the characteristic axis of the tool determined in real-time, and the distance of said 2D image plane relative to the working end of the tool being such that the real-time image generated in the 2D image plane corresponds at least approximately to a vision of the target area from the point of view of an observer situated at or near a part of the tool or said characteristic axis of the tool;

h) the image generated along said plane including indications of the position of the target to be treated by said tool and/or the position of the functional characteristic axis of said tool in said image as well as the dimensions of the tool in a direction perpendicular to said functional characteristic axis.

According to a first preferred alternative, the inclination of said 2D image plane relative to the direction or the characteristic axis of the tool, and the distance of said 2D image plane relative to the working end of the tool are such that the image generated in the 2D image plane corresponds at least approximately to a vision of the target area from the point of view of an observer situated at said working end of the tool, and whose direction of view is coincident with or parallel to the direction or the characteristic axis of the tool, whereas said 2D image includes indications of the position of the target to be treated by said tool and/or the point of coincidence of the characteristic axis of the tool with said 2D image plane and possibly also with the section of the tool along said plane.

In a second preferred alternative, the cutting plane along which the 2D image is generated is at least parallel to the characteristic axis of the tool. Possibly, this plane is also coincident with said characteristic axis of the tool. In this case, the image being displayed is similar to the image that a user would see in a direction of view perpendicular to that of the characteristic axis of the tool, whereas the position of the characteristic axis of the tool is indicated in said image by two lines parallel to said axis and situated at a distance from each other at least corresponding to the tool size perpendicular to said characteristic axis, and the position of the target to be treated by said tool is also indicated.

It is important to notice that the acquisition of the volumetric (3-D) ultrasound images is made at the same time, i.e. contemporary to the tracking of the probe and of the tool and to the registration of the tracking coordinates with the coordinates of the said volumetric images, so that the images shown on the 2D image planes is a real-time image, which time delay relatively to the effective one is limited to the time needed for the computation. Computational burden and computational times are dramatically low relatively to prior art systems particularly due to the fact that only ultrasound data are used for generating some sort of endoscopic images which are non video (i.e. surface images) and that the registration step can be carried out at the beginning of the session only once and eventually may be repeated at certain time intervals.

No endoscopic or video device is needed further to the ultrasound probe and to the tracking means.

As it will appear also from the following description using a 3-D probe reduces further the computational burden because the probe may be held at a fixed position and the tracking data to be determined are only the ones of the interventional tool.

Advantageously, the device is provided in combination with a rod or needle-like element and the characteristic direction or characteristic axis is the longitudinal axis of said rod or needle or a direction or axis parallel to said longitudinal axis, whereas the working end is the rod or needle insertion end into the target area.

A position and orientation identification and detection marker is associated with the tool, and may be advantageously arranged to be coincident with the characteristic axis or an axis parallel thereto or in a predetermined position relative thereto. Particularly in the case of a biopsy needle or the like, the marker may be located at the tip or rear end of the needle or the like.

Advantageously, according to an improvement, in order to account for and detect any bending of the tool, at least two identification and detection markers are associated therewith, which are located at a certain distance from each other along said direction or said characteristic axis or along an axis parallel to said characteristic axis. The marker/s cooperate with detection means of a system for determining and/or tracking the position and orientation of the tool relative to a predetermined reference system.

In one embodiment, the device further comprises a monitor and means for displaying images on said monitor, which means allow simultaneous, side-by-side or alternate display of images of the target area defined by at least one image plane coincident or parallel to the direction or characteristic axis of the tool and by at least one image plane having the predetermined inclination relative to the direction or the characteristic axis of the tool and the predetermined distance from the working end of the tool.

Advantageously, the sequence of 3D images is acquired by an ultrasonic probe, whereas the position in space of the acquired image relative to a reference system is determined by probe position and displacement detection systems.

Particularly a volumetric probe is advantageously used for acquiring the sequence of 3D images.

Referring to the units that compose the device of the present invention, either one of the two following solutions can be used for detecting the relative position of the probe and the tool.

In a first embodiment, the means for determining the position and orientation of the tool and particularly the biopsy needle, i.e. the characteristic axis thereof, are the 3D imaging system itself, i.e., in this special case, the means for acquiring the sequence of 3D ultrasonic images. The detected volumetric images also include the image of the tool when the latter is within the field of view, and this image of the tool is used to determine, thanks to the markers, the position and orientation of the tool, i.e. its characteristic axis, relative to the 3D image and hence the position and orientation of the tool in the anatomic region being imaged.

This technique is not limited to the ultrasonic imaging use. It can be also applied to X-ray or CT imaging. In this case the ring would be displaced instead of the patient table, and the CT images would display both the diseased tissue and the tool, i.e. the biopsy needle.

In the second embodiment, a tracking system is used for detecting the position and orientation of the probe and the tool, particularly the characteristic axis thereof. The tracking system allows the positions of the probe and tool, e.g. a needle, to be related to each other, to define the cut plane in the tool path. Several different tracking systems are current available, of either electromagnetic or optical type. The remarkable advantage of an electromagnetic system consists in that it has very small markers, consisting of micro-receivers that may be also placed at the tip of the needle. A tracking system adapted for use with a needle is the one sold by Ascension Technology with the trade name PCIBird.

These micro-receivers are used in combination with the transmitter to define the position of the probe and the needle on space and to determine the cut plane. Advantageously, two micro-receivers are associated with the needle at the tip and the rear, to accommodate any bending. Such bending would create curved surfaces formed by the volume 4D.

Concerning the tools for which the method and device of the invention are particularly suitable, these may be of the minimally invasive type, such as infiltration syringes, biopsy tools, thermoablation needles, HIFU rays. A possible method for standardizing all needle families consists in providing a custom "spindle" equipped with a receiver to be used as an insertion tool designed to be fitted with the special needle for the required procedure.

The probe, particularly of volumetric type, may be either convex or linear and will be advantageously able to generate a 3D image of the required size. The minimum volume rate required to obtain effects is 4 volumes/sec.

A volumetric probe may be as disclosed in EP 1 681 019 and in EP 1 167 996 by the applicant hereof.

The invention also relates to a method for guiding surgical tools by ultrasonic imaging using the above described device, which method includes the steps of:

a) acquiring a time sequence of 3D ultrasonic images of a target area;

b) defining a direction or a characteristic working axis for the tool;

c) defining the position of a working or functional end of the tool along said direction or said characteristic axis;

d) determining the relative position in space of each of the 3D images of the time sequence of images and the direction or characteristic axis of the tool for each of said 3D images;

e) defining, for one or more of the 3D imaged acquired in the time sequence, a plane of a 2D image which intersects the corresponding 3D image and has a predetermined inclination relative to the direction or the characteristic axis of the tool and a predetermined distance from the working end of the tool with reference to the orientation and position of the tool upon acquisition of the corresponding 3D image;

f) using the data of the corresponding 3D image of the sequence of 3D images to generate an image along said 2D image plane;

g) the inclination of said 2D image plane relative to the direction or the characteristic axis of the tool, and the distance of said 2D image plane relative to the working end of the tool being such that the image generated in the 2D image plane corresponds at least approximately to a vision of the target area from the point of view of an observer situated at or near a part of the tool or said characteristic axis of the tool;

h) the image generated along said plane including indications of the position of the target to be treated by said tool and/or the position of the functional characteristic axis of said tool in said image.

Particularly relevant for the present invention is the fact that steps a) to c) are contemporary and carried out in real time.

So each 3-D image is a real time ultrasound image and the position and orientation of the tool is also real-time and related to the corresponding 3-D image. Thus also the steps and the results of the steps indicated above with d) to h) are essentially carried out in real-time, if considering very short computational times. Thus the 2-D image displayed and corresponding to a certain plane as defined in steps g) to h) is practically a real-time image. The time shift between the effective position of the tool in the real world and the one determined by the method being infinitesimal and corresponding to the time needed by the system to carry out the computational steps.

As additional information, said image may also include indications about the dimensions of the tool in a direction perpendicular to said functional characteristic axis.

According to a preferred alternative, the cutting plane along which the 2D image is generated has such an inclination that the image being generated corresponds to the one that a user would see if he/she were situated at said working end of the tool in a direction of view coincident or parallel to the direction or the characteristic axis of the tool, whereas said 2D image would include an indication of the position of the target to be treated by said tool and/or the point of coincidence of the characteristic axis of the tool with said plane of the 2D image and possibly also the section of the tool along said plane.

Advantageously, the method is carried out in combination with tools including a rod or needle-like element and the characteristic direction or characteristic axis is the longitudinal axis of said rod or needle or a direction or axis parallel to said longitudinal axis, whereas the working end is the rod or needle insertion end into the target area.

In this case the 2D image plane may be perpendicular to the direction or characteristic axis of the tool.

In a further alternative, the cutting plane along which the 2D image is generated and displayed is parallel to and possibly also coincident with said characteristic axis of the tool. In this case, said image contains indications about a possible range for positioning the needle or tool, i.e. the characteristic axis of the needle or tool, which range is delimited by two parallel lines spaced to an extent at least corresponding to the detection accuracy of the system. In practice, the two lines delimit the image area in which the image of the tool is expected to appear.

In order to determine the position and orientation of the tool with reference to an axis and particularly to the characteristic or working axis thereof, one position detection and identification marker has to be placed on the tool in a predetermined position relative to the tool shape.

Preferably, according to an improvement, at least two identification and detection markers are associated with the tool, and are located at a certain distance from each other along said direction or said characteristic axis or along an axis parallel to said characteristic axis, which markers cooperate with detection means of a system for determining the position and orientation of the tool relative to a predetermined reference system.

As mentioned above in greater detail, several different systems may be used for determining the position and orientation of the tool relative to the image volume.

One solution consists in using the tool image that appears in the acquired volumetric images.

The second solution, which has also been described above, includes a tracking system which uses sensors or transponders on the tool and the ultrasonic probe to determine their position and orientation relative to a reference coordinate system predetermined by the tracking system itself. According to an improvement of the method of the invention, the sequence of 3D images is acquired by an ultrasonic probe, whereas the position in space of the acquired image relative to a reference system is determined by probe position and displacement detection systems.

Advantageously, the sequence of 3D images is acquired using a volumetric probe.

Considering the above characteristics of the method of the invention, such method is thus based on the concept of using the image planes generated by a volumetric probe to drive an tool, such as a needle, using a tracking system, for optimized selection of both the position of the needle relative to the probe and the image plane to be associated with the needle. In this case, the image plane of the probe may not be coplanar with the image plane of the needle.

In other words, the volumetric probe is used to generate a real-time 4D volume. The mutual positions of the probe and the needle are defined using the tracking system. These relative position coordinates are used to generate a plane to be associated with the needle, by cutting off the acquired volumes according to the needle position. A real-time image is thus obtained, which is associated with the needle. The volumetric probe is only used as a data generator, whereas the needle is used both for the percutaneous procedure and as a probe. Thus, by simply moving the needle, the user can display the target and easily select the type of insertion.

According to another characteristic, the device of the invention may provide simultaneous, side-by-side or alternate display of images of the target area defined by at least one image plane coincident or parallel to the direction or characteristic axis of the tool and by at least one image plane having the predetermined inclination relative to the direction or the characteristic axis of the tool and the predetermined distance from the working end of the tool.

Images may be also possibly displayed according to different image planes, intersecting the volumetric image with different inclinations and at different points.

In at least one of the images, the position of the tool is indicated by a symbol which is well differentiated from the image of the target area.

The above description clearly shows the advantages and differences of the method and device of the present invention as compared with standard neurosurgery navigators. In prior art navigation and guide systems, the surgical tool or the ultrasound probe is associated with an image obtained from a pre-acquired volume and not a real-time image associated with the needle.

Conversely, the present invention uses a real-time imaging source, to associate the position of the tool and the image of its path. On the other hand, the tracking system may be the imaging source itself, with the tool and its position and orientation in the imaging volume being identified in real time.

Further improvements will form the subject of the dependent claims.

The characteristics of the invention and the advantages derived therefrom will be more apparent from the following description of non-limiting embodiments, and as illustrated in the drawings.

BRIEF SUMMARY

A device and method for guiding surgical tools by ultrasonic imaging having means for acquiring a time sequence of 3D ultrasonic images of a target area, means for determining and tracking the position and orientation of a surgical tool and means for defining the direction of a characteristic axis of the tool corresponding to the detected position and orientation of the tool. The device further having means for determining the position of a working end of the tool along the characteristic axis, means for determining the relative position in space of each 3D image and the direction of the characteristic axis corresponding to each 3D image, and means for generating a 2D image defined by an image plane that intersects the corresponding 3D image of said time sequence.

One object of the present invention is to provide an improved device and method for guiding surgical tools.

Related objects and advantages of the present invention will be apparent from the following description.

DETAILED DESCRIPTION OF THE DISCLOSURE

For the purposes of promoting an understanding of the principles of the invention, reference will now be made to the embodiments illustrated herein and specific language will be used to describe the same. It will nevertheless be understood that no limitation of the scope of the invention is thereby intended. Such alterations and further modifications in the described processes, systems or devices, any further applications of the principles of the invention as described herein, are contemplated as would normally occur to one skilled in the art to which the invention relates, now and/or in the future.

Figure 1:
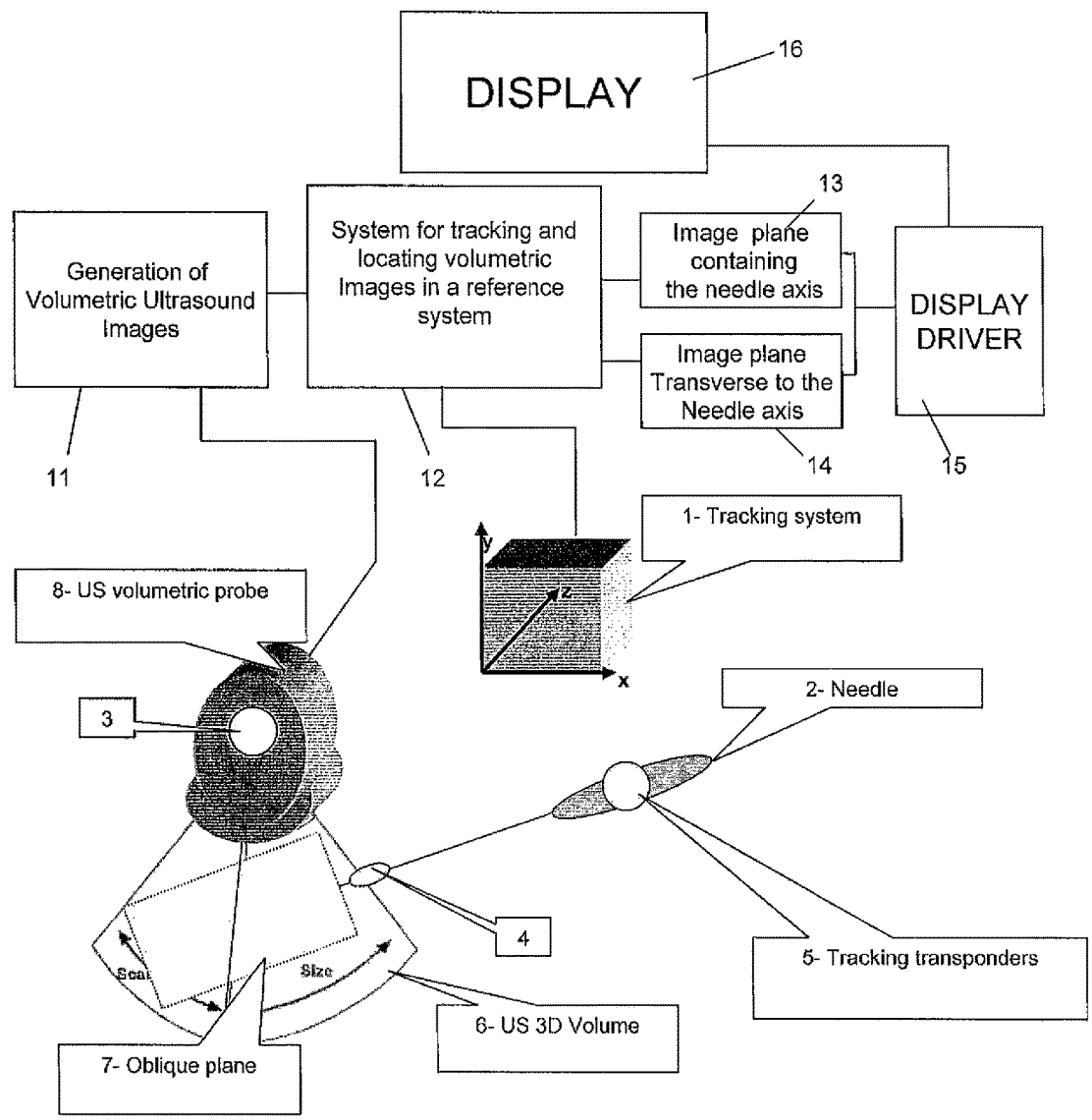
FIG. 1 is a schematic block diagram of the structure of a system of the invention, in which said system is provided in combination with a biopsy needle.

A system for guiding surgical tools by real-time ultrasonic imaging is very schematically shown in FIG. 1.

Numeral 8 designates an ultrasonic scan probe which is connected to a probe control unit for ultrasonic imaging and particularly for generating volumetric ultrasound images. A variety of volumetric ultrasound imaging methods are known. According to a known method, the probe is provided in combination with a tracking system which detects the position, orientation and displacement of the probe. A succession of ultrasound images is acquired as the probe is moved, said images being grouped into a 3D image composed of the various 2D images acquired at different probe positions along the displacement path, which positions are detected by the tracking system. Thus, the 2D images can be arranged in relative order to form a 3D image.

Tracking systems are known and widely used for the purpose of acquiring a 3D ultrasound image. An example of tracking system is the system sold by Ascension Technology with the trade name PCI Bird which is incorporated in a currently available product, sold by the owner hereof with the name of "Virtual Navigator".

In the scheme of FIG. 1, the tracking system is represented by the coordinate system designated by numeral 1. The tracking system actually defines the various positions of the probe 8 with reference to a predetermined initial reference point and is thus the operating unit that defines a reference system describing the probe displacement space.

In principle, there is no limitation as for the type of probe to be used, provided that it can cover a slice area large enough to contain the image to be acquired. Nonetheless, as shown in FIG. 1, advantages are achieved from using a volumetric probe. A volumetric probe may be as disclosed in EP 1 681 019 and in EP 1 167 996 by the owner hereof Thus, when the size of the subject to be imaged by ultrasound allows to do so, the probe is not required to be manually displaced by the operating personnel or a specially dedicated device. In other cases, the volumetric probe can be displaced less often and to few different positions, in which it can be held during automatic acquisition of the volumetric image that the probe can generate without being displaced.

In this case, the tracking system 1 is only used to define the different probe position/s in the space described by the reference system generated or defined by the tracking system 1 itself.

The tracking systems require at least one detector to be mounted to the element whose displacement or position is to be monitored, which marker/detector, with reference to the tracking system used herein, is a transponder. A transmitter-receiver unit can detect the marking transponder and determine the probe position. The marker means associated with the probe 8 are designated by numeral 3.

Numeral 6 designates the volumetric image acquired by the volumetric probe 8.

Numeral 2 designates a surgical tool and particularly a needle or similar elongate, rod-like element. These tools may include, for example, biopsy needles, cannulas for insertion of a variety of devices, thermoablation needles or the like.

The needle or rod-like element has a characteristic functional axis, and in this case this axis is the axis of the needle which coincides with the insertion axis. Different types of tools may have different characteristic functional axes. For example, in the case of a surgical knife, the characteristic working axis may be the cutting edge of its blade. The characteristic functional axis of a particular type of tool can be determined in an intuitive and simple manner.

The needle 2 may carry a single sensor or marking transponder, which is sufficient to determine the position of the tool and its orientation, particularly with reference to the characteristic working or functional axis of said needle which, as mentioned above, is the central longitudinal axis of the needle.

However, according to the improvement of the figures, the tool, i.e. the needle 2 carries two or more sensors or marking transponders, designated by numerals 3, 4. This improvement allows detection of any needle bending, which can be thus accounted for while operating the system.

Therefore, in the case of the needle 2 of the figures, two transponders are located at a certain distance from each other, coincident with the needle axis, and can be used to determine the needle orientation with particular reference to the insertion direction, as well as any deformation, particularly bending or curving of the needle. When a transponder is mounted directly to the tip or at a predetermined distance therefrom, the position of the needle tip can be determined upon insertion into the body under examination.

The sensor or transponder at the tip of the needle 2, here the transponder 4, shall not necessarily be placed at the tip but, as mentioned above, it may be located at a predetermined known distance from the tip. In this case, once the position of the transponder 4 has been detected, the position of the tip may be determined by a simple arithmetic operation.

Numeral 7 designates a cutting plane of the 3D image that has a predetermined inclination relative to the characteristic functional axis, i.e. the longitudinal central axis, i.e. the direction of insertion of the needle 2.

A 2D image of the object is generated along said cutting plane, using the image data of the 3D image.

This process consists in determining the subset of voxels of the 3D image that falls within the predetermined cutting plane 7, to generate a 2D image. This may occur in a known manner, as disclosed for instance in the above mentioned patent applications by the applicant hereof, and particularly in EP 1 167 996.

Processing occurs in a control and processing unit typically incorporated in ultrasonic imaging apparatus, which substantially consists of a processing unit that stores and executes special ultrasound apparatus control programs for transmitting and receiving ultrasound signals, for focusing the ultrasound signals transmitted by the probe and the ultrasound signals received by the probe upon reflection of the transmitted signals, for converting the received signals into image data and for generating and displaying images on a monitor, as well as for monitoring the execution of other operations that depend on the ultrasound signal acquisition and processing mode being used. The processing unit also controls the tracking system, which may be provided as software or dedicated hardware controlled by said software.

In FIG. 1, the processing unit is designated by its functional blocks only, which are generally used to execute the operations of the present invention. Thus, the block 11 generally includes all hardware and software units required for 3D imaging (see also EP 1 681 019 and EP 1 167 996). Thanks to the tracking system, the 3D image is assigned a well-defined position in a reference Cartesian system, which is defined by the tracking system that detects the position of the probe 8. The tracking system simultaneously detects the position of the needle or other tool 2 and the orientation of the characteristic functional axis of such tool 2 with reference to the same reference system defined by the tracking system. This will provide well-defined relative positions between the volumetric image and the position and orientation of the tool 2, i.e. the characteristic functional axis thereof.

In these conditions, a cutting plane may be defined in the 3D or volumetric image generated by the probe 8, which plane has a predetermined inclination relative to the characteristic functional axis of the tool 2.

Multiple cutting planes may be also defined, having predetermined and different positions and orientations relative to said characteristic functional axis of the tool 2.

Particularly, referring to the needle, a cutting plane may be defined, which is oriented perpendicular to the characteristic functional axis of the tool 2 and is at a predetermined distance from the internal or front end tip, with reference to the direction of insertion of the needle. In this case, the image generated along said cutting plane and reconstructed from the volumetric image data, i.e. the voxels that fall within such cutting plane will be as viewed by an observer situated at the tip of the needle and looking towards the longitudinal axis of the needle in the direction of insertion of the latter.

Alternatively to or in combination with the above, images may be also generated along different cutting planes.

A possible additional cutting plane might be the plane that contains the longitudinal axis of the needle 2, with the path of the needle into the body under examination being thus visible.

The images obtained along the various cutting planes may be displayed in succession, i.e. alternate to each other or in side-by-side or simultaneous arrangement.

This condition is shown by the functional blocks 12, 13 and 14, which designate all hardware and software units required to define the above mentioned cutting planes and generate images along said cutting plane, as well as simultaneously or alternately display them using display drivers 15 on the display 16.

The use of a volumetric probe 8 allows the above process to be accomplished in a very short time, wherefore imaging may be deemed to occur in real time.

Figure 2:
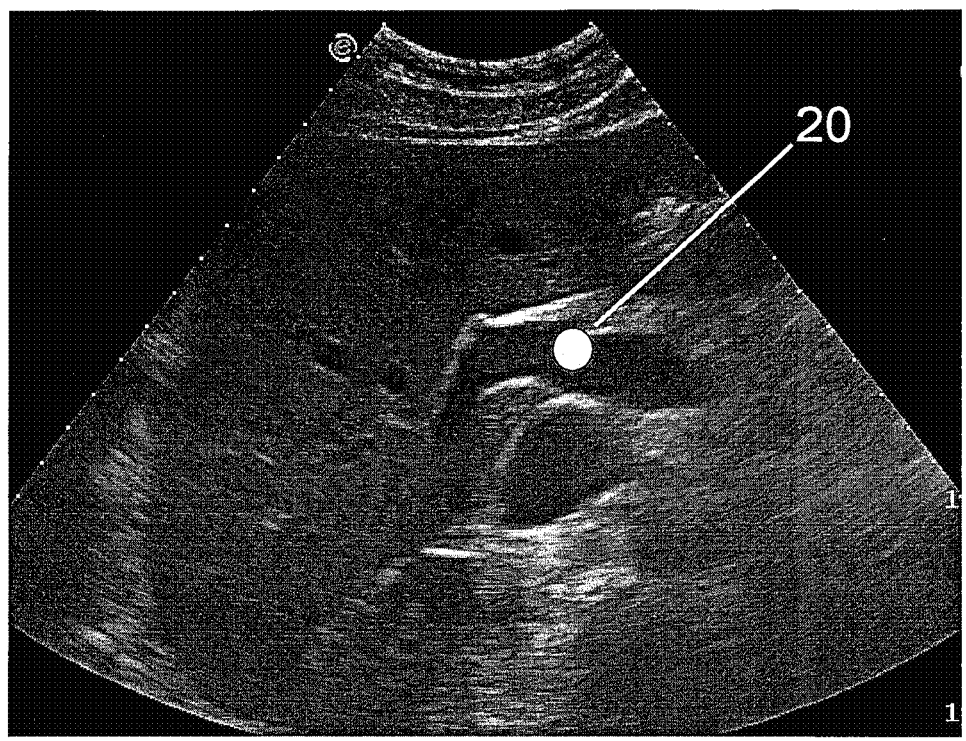
FIG. 2 shows a tissue image of the present invention corresponding to the central frame of the succession of frames that cover the acquisition volume of a volumetric probe.

FIG. 2 shows the central 2D image of a volumetric image obtained using a volumetric probe as disclosed in EP 1 681 019 and EP 1 167 996 respectively.

Figure 3:
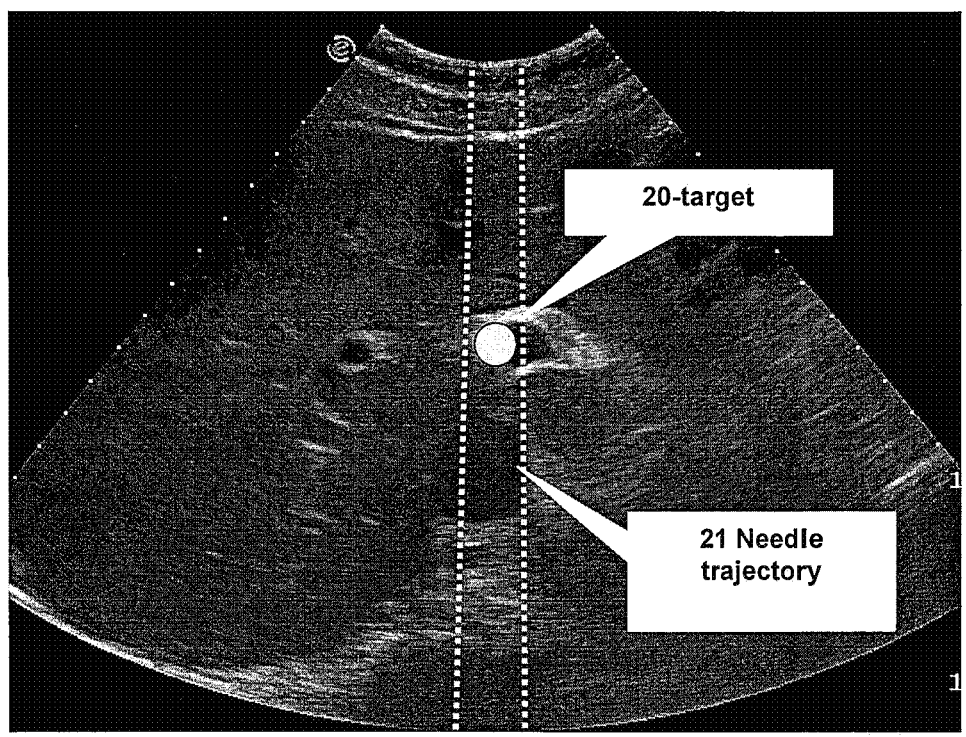
FIG. 3 shows an image of the same acquired volume, with the image plane being oriented relative to the characteristic working axis of the needle, and particularly parallel to the needle axis.

FIG. 3 shows a 2D image along a plane parallel to the axis of the needle 2, containing an indication of the target 20 to be reached and treated by the needle and the trajectory of the needle 21, i.e. an image as viewed from the needle, and not from the probe. The trajectory of the needle 21 is indicated in the form of a channel delimited by longitudinal dash lines. These lines are parallel to the needle axis and their spacing is at least equal to the external diameter of the needle 2.

As clearly shown herein, in this case the needle guiding function does not rely on an image of the needle in the body from the point of view of the probe position, but on the needle trajectory that is indicated in the 2D image that corresponds to the image of one of the cutting planes containing the longitudinal axis of the needle.

The image of FIG. 2 may also contain indications about the incidence point of the longitudinal axis of the needle and the 2D image plane and possibly the cross-section of the needle, using the 2D image plane as a cutting plane.

Alternative to or in combination with the above, the cutting plane of the 3D image, i.e. the 2D image may be a plane parallel to the longitudinal axis of the needle, but situated at a predetermined distance from such axis.

According to an improvement, a traditional image of the body being examined and the needle may be also displayed in either alternate or simultaneous, side-by-side arrangement.

Figure 4:
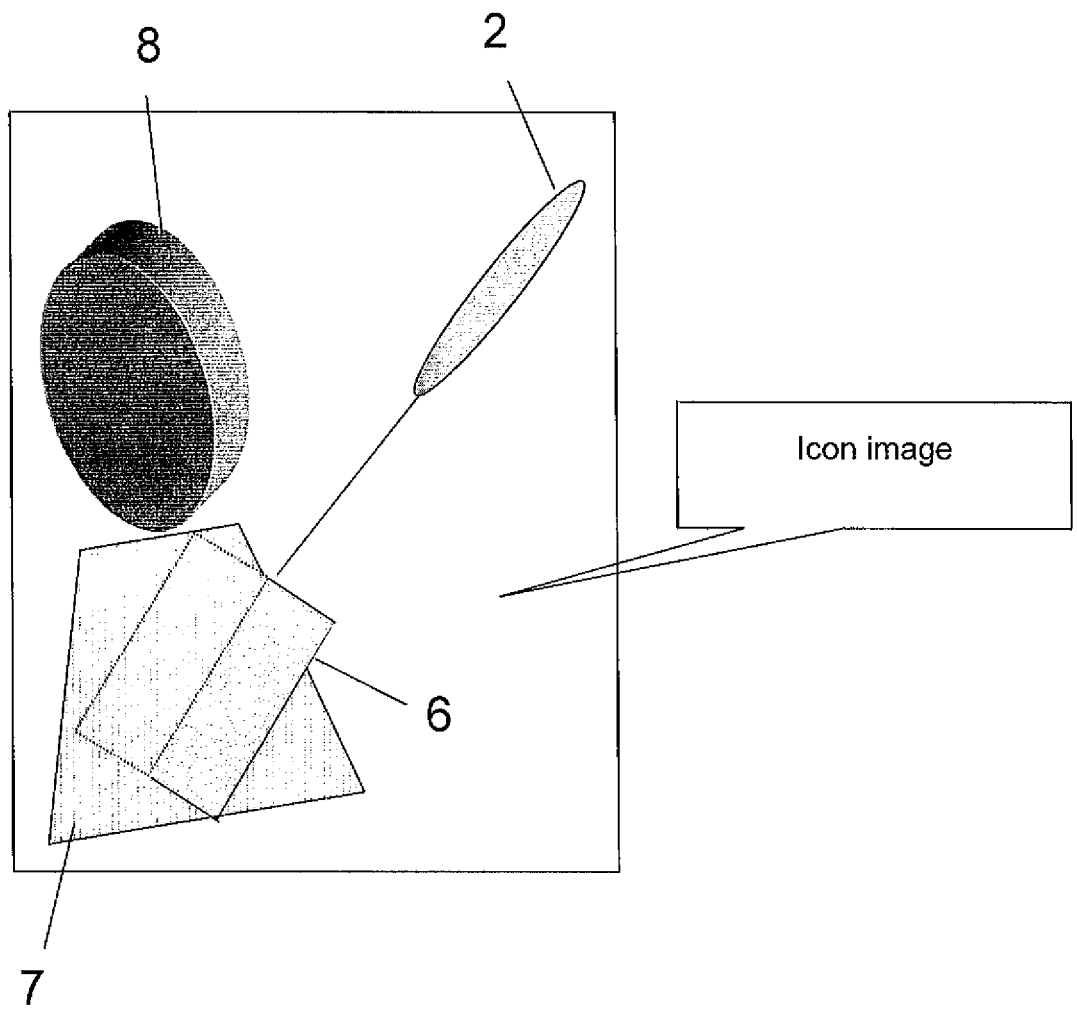
FIG. 4 shows a schematic icon representing the relative positions and orientations of the needle and the probe.

In yet another improvement, as shown by way of example in FIG. 4, in order to visually check the position of the needle 2 or tool relative to the probe, i.e. to the central longitudinal plane parallel to the long side of the array of electroacoustic transducers of the probe 8 which, in the case of volumetric probes, is parallel to the axis of oscillation of the array of transducers, a schematic image may be displayed in which the probe, said plane, the tool and the predetermined cutting plane/s are indicated in their proper relative positions as detected by the tracking system. By this arrangement, the user may simply ascertain proper operation of the system at a glance.

The schematic icon image may be displayed at the same time as the ultrasound images, side by side with or in a separate window, partially overlapping one or more of the ultrasound images being displayed. If one or more ultrasound images are displayed, each for a cutting plane having a predetermined position and a predetermined orientation, i.e. a predetermined inclination relative to the axis of the needle 2, i.e. the characteristic functional axis of the tool, then a corresponding schematic icon image may be displayed for each of said images, in which the probe and the tool, as well as the corresponding cutting plane, are in the relative positions corresponding to the ultrasound image.

Referring to the above system and method, a variant of the needle tracking means may be provided for determining the position and orientation of the needle relative to the acquired volumetric images.

According to such variant, the position and orientation of the tool relative to the volumetric images may be determined using the needle image appearing in such volumetric images, instead of providing an external tracking system that detects both the position and orientation of the tool and the position and orientation of ultrasound probe. Once more, the provision of a position identification and indication marker having a predetermined position relative to the shape and size of the tool, particularly the needle, allows the tool to be located within the 3D image, wherefore a cutting plane may be defined in the 3D image, which has predetermined orientation and position relative to the tool, along which cutting plane a 2D image is generated whose pixels are the voxels of the imaging volume which fall within said cutting plane. Therefore, regardless of the means that are used for determining the position and orientation of the tool and/or the characteristic axis thereof, the next steps are the same as in the example in which an external system is used for tracking the position and orientation of the tool and the position and orientation of the ultrasound probe. It shall be obviously noted that the term cutting plane is indented to also mean a thin slice, i.e. a volume delimited by two parallel cutting planes very close to each other within the resolution of the ultrasonic imaging system. This interpretation will be well understood by those skilled in the art, who are perfectly aware that any reference to a 2D image will relate to an image of an area having a predetermined volume, which is formed of a thin slice crossing the subject under examination.

It has to be noticed that ultrasound 3-D images and probe and tool tracking are carried out at the same time and in real-time. This means that while inserting and displacing the interventional tool the probe acquires a sequence of 3D (three dimensional or volumetric) images of the zone in which the probe is present. Thus to a certain instant a specific 3D-image is associated and to it a specific tracking data for the tool and of the probe are also univocally associated. This image data and the corresponding tracking data of the tool and eventually of the probe are used for constructing by computation the image or images along one or more specific 2D planes (two dimensional planes) having a predetermined orientation in the space defined by the corresponding 3D image and relatively to the tool tip and orientation. So the 2D image or images shown are essentially real time images. The time shift between the effective tool position in the real world and the one as determined by the acquired image and tracking data is limited to the time needed for the acquisition of the image and tracking data and for computing the said data in order to generate the 2D image or images. These times are relatively short so that the inaccuracy is infinitesimal and can be disregarded. Furthermore it has also to be considered that in the above kind of intervention the tool is normally displaced very carefully and at very low speed and often also step by step, so that the already infinitesimal time shift can be disregarded completely for no having any significant practical effect.

Concerning the system and method of the present invention, a remarkable advantage has to be noted as compared with prior art systems and methods.

A true real-time guiding method and system is provided which can furnish a special kind of endoscopic view which is not limited to a video (surface) image, but which goes beyond the visible surfaces and allows the user to efficiently and precisely guide the tool by having a visual and spontaneous feedback of the manipulation of the tool.

With the invention, the body can be penetrated by the tool, i.e. the needle, from the side opposite the one with the ultrasound probe. In clinical terms, this means that while at present the ultrasound scanning window and the needle access must be located in a well-defined area of the body under examination, possibly providing the best results in terms of both imaging and tool, i.e. needle, insertion, the invention allows simultaneous selection of the best ultrasound scanning window and the best access, because these conditions are independent of each other.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected. It is also contemplated that structures and features embodied in the present examples can be altered, rearranged, substituted, deleted, duplicated, combined, or added to each other. The articles "the", "a" and "an" are not necessarily limited to mean only one, but rather are inclusive and open ended so as to include, optionally, multiple such elements.

What is claimed is:

1. A device for guiding surgical tools by real-time ultrasonic imaging, which device comprising:
    a) an ultrasound system for acquiring in real-time a sequential plurality of 3D ultrasonic images of a target area;
    b) a system for determining in real-time and tracking of the position and orientation of a surgical tool and for defining in real-time the direction of a characteristic axis of the tool corresponding to the detected position and orientation of the tool;
    c) a unit for determining in real-time the position of a working end of the tool along said direction of said characteristic axis;
    d) a system for determining the relative position in space of each 3D ultrasonic image and the direction of the characteristic axis of the tool corresponding to each 3D ultrasonic image; and
    e) a unit for generating, for one or more of the 3D ultrasonic images acquired sequentially, a real-time 2D image defined by a 2D image plane that intersects a corresponding 3D ultrasonic image, which 2D image plane is perpendicular to the direction of the characteristic axis of the tool determined in real-time and is spaced a predetermined distance forward of the working end of the tool with reference to the orientation and position of the tool upon acquisition of the corresponding 3D ultrasonic image, said 2D image being generated using the corresponding 3D ultrasonic image;
    f) a monitor and a unit for displaying said real-time 2D image on said monitor, said real-time 2D image being from the point of view of the tool;
    wherein the intersection of the characteristic axis of the tool and the 2D image plane is indicated in said 2D image; and
    wherein the position of the target to be treated by said tool is also indicated in said 2D image.

2. The device as claimed in claim 1, wherein the tool is a needle-like element and the characteristic axis is the longitudinal axis of said needle, wherein the working end is the needle end insertable into the target area.

3. The device as claimed in claim 1, further comprising a marker that is associated with the tool for identifying and detecting the position and orientation of the tool, the marker cooperates with the system for determining and tracking the position and orientation of the tool relative to a predetermined reference system.

4. The device as claimed in claim 1, further comprising at least two or more identification and detection markers that are associated with the tool and are located at a certain distance from each other along an axis parallel to said characteristic axis, the markers cooperate with the system for determining and tracking the position and orientation of the tool relative to a predetermined reference system.

5. The device as claimed in claim 1, wherein the unit for displaying allows simultaneous, side-by-side or alternate display of images of the target area defined by at least one image plane parallel to the direction of the characteristic axis of the tool and by said 2D image plane perpendicular to the direction of the characteristic axis of the tool and spaced from the working end of the tool.

6. The device as claimed in claim 1, wherein the sequence of 3D images is acquired by an ultrasonic probe, wherein the position in space of the acquired image relative to a reference system is determined by probe position and displacement detection systems.

7. The device as claimed in claim 1, wherein the system for acquiring a time sequence of 3D ultrasonic images of a target area is a volumetric probe.

8. The device as claimed in claim 1, further comprising a system for detecting and tracking the position and orientation of the tool with reference to the 3D ultrasonic images that determine said position and said orientation from the tool images appearing in the sequence of the 3D ultrasonic images of the area being scanned.

9. The device as claimed in claim 1, further comprising an external system for tracking the position and orientation of the tool, the external system defining a reference coordinate system and, in such system, tracking the relative positions and orientations of the tool and an ultrasound probe of the ultrasound system.

10. The device as claimed in claim 1, wherein the unit for generating a real-time 2D image is configured to generate a real-time 2D image of a target area that does not contain said tool and therefore the tool is not displayed in said 2D image.

11. The device as claimed in claim 1, wherein said system for determining in real-time and tracking of the position and orientation of a surgical tool is said ultrasound system.

12. A method for guiding a surgical tool by ultrasonic imaging, comprising the steps of:

a) acquiring in real-time a sequential plurality of 3D ultrasonic images of a target area;

b) defining in real-time an orientation and position of the tool and a direction of a characteristic working axis of the tool;

c) defining in real-time the position of a working end of the tool along said direction of said characteristic axis;

d) determining the relative position in space of each of the 3D ultrasonic images of the time sequence of images and the direction of the characteristic axis of the tool for each of said 3D images;

e) defining, for at least one of the 3D ultrasonic images acquired in the time sequence, a 2D image plane which intersects the corresponding 3D ultrasonic image and is perpendicular to the direction of the characteristic axis of the tool determined in real-time and is spaced a predetermined distance forward of the working end of the tool with reference to the orientation and position of the tool upon acquisition of the corresponding 3D ultrasonic image;

f) generating a real-time 2D image using the corresponding 3D ultrasonic image of the sequence of 3D ultrasonic images along said 2D image plane;

wherein the position of the characteristic axis of the tool is indicated in said 2D image;

and wherein the 2D image includes indications of the position of the target to be treated by said tool.

13. The method as claimed in claim 12, wherein the tool is a needle-like element and the characteristic axis is parallel to the longitudinal axis of said needle, wherein the working end is the needle end insertable into the target area.

14. The method as claimed in claim 12, wherein a marker is associated with the tool for identifying and detecting the position and orientation of the tool, the marker cooperates with a detection system for determining and tracking the position and orientation of the tool relative to a predetermined reference system.

15. The method as claimed in claim 12, wherein at least two identification and detection markers are associated with the tool and are located at a certain distance from each other along an axis parallel to said characteristic axis, the markers cooperate with a detection system for determining and tracking the position and orientation of the tool relative to a predetermined reference system.

16. The method as claimed in claim 12, further comprising the step of providing simultaneous, side-by-side or alternate display of images of the target area as defined by at least one image plane parallel to the direction of the characteristic axis of the tool and by at least one image plane perpendicular to the direction of the characteristic axis of the tool and spaced from the working end of the tool.

17. The method as claimed in claim 16, wherein in at least one of the displayed images, the position of the tool is indicated by a symbol which is differentiated from the image of the target area.

18. The method as claimed in claim 17, wherein the sequence of 3D ultrasonic images is acquired by an ultrasonic probe, wherein the position in space of the acquired image relative to a reference system is determined by probe position and displacement detection systems.

19. The method as claimed in claim 18, wherein a volumetric probe is used for acquiring the sequence of 3D ultrasonic images.

20. The method as claimed in claim 19, comprising the step of providing a system for detecting and tracking the position and orientation of the tool with reference to the 3D ultrasonic images.

21. The method as claimed in claim 19, comprising the step of providing an external system for tracking the position and orientation of the tool and the characteristic axis of the latter and the ultrasound probe, the external system defining a reference coordinate system and tracking the relative positions and orientations of the tool and the ultrasound probe.

22. The method as claimed in claim 12, wherein said 2D image is of a target area that does not contain said tool and therefore the tool is not displayed in said 2D image.

23. The method as claimed in claim 12, wherein said defining in real-time an orientation and position of the tool includes defining with ultrasound in real-time an orientation and position of the tool.

24. A device for guiding surgical tools by real-time ultrasonic imaging, which device comprising:

a) an ultrasound system for acquiring in real-time a sequential plurality of 3D ultrasonic images of a target area;

b) a system for determining in real-time and tracking of the position and orientation of a surgical tool and means for defining in real-time the direction of a characteristic axis of the tool corresponding to the detected position and orientation of the tool;

c) a unit for determining in real-time the position of a working end of the tool along said direction of said characteristic axis;

d) a system for determining the relative position in space of each 3D ultrasonic image and the direction of the characteristic axis of the tool corresponding to each 3D ultrasonic image; and e) a unit for generating, for one or more of the 3D ultrasonic images acquired sequentially, a real-time 2D image defined by a 2D image plane that intersects a corresponding 3D ultrasonic image, which 2D image plane is perpendicular to the direction of the characteristic axis of the tool determined in real-time and is spaced a predetermined distance forward of the working end of the tool with reference to the orientation and position of the tool upon acquisition of the corresponding 3D ultrasonic image, said 2D image being generated using the corresponding 3D ultrasonic image;

wherein the 2D image generated along said plane includes indications of the position of the target to be treated by said tool and the position of the characteristic axis of said tool in said 2D image;

and wherein the position of the target to be treated by said tool is also indicated in said 2D image.

* * * * *